United States Patent [19]

McCombie

[11] 4,456,609

[45] Jun. 26, 1984

[54] (5R, 6S, 8R-6-(1-HYDROXYETHYL)-2-(2-[METHYLAMINOCARBONYL]-ETHYLTHIO)-PENEM-3-CARBOXYLIC ACID

[75] Inventor: Stuart W. McCombie, West Orange, N.J.

[73] Assignee: Schering Corporation, Kenilworth, N.J.

[21] Appl. No.: 462,723

[22] Filed: Jan. 31, 1983

[51] Int. Cl.³ .................. C07D 499/00; A61K 31/425
[52] U.S. Cl. ............................. 424/270; 260/245.2 R
[58] Field of Search ..................... 260/239.1, 245.2 R; 424/270

[56] References Cited

U.S. PATENT DOCUMENTS

| 4,260,618 | 4/1981 | Christensen et al. | 260/245.2 R |
| 4,301,074 | 11/1981 | Christensen et al. | 260/245.2 R |
| 4,374,844 | 2/1983 | McCombie | 260/245.2 R |
| 4,386,030 | 5/1983 | Christensen et al. | 260/245.2 R |

FOREIGN PATENT DOCUMENTS 2074563A  11/1981  United Kingdom .

*Primary Examiner*—Nicholas S. Rizzo
*Attorney, Agent, or Firm*—Gerald S. Rosen

[57] ABSTRACT

There is disclosed the antibacterial 5R,6S,8R-6-(1-hydroxyethyl)-2-(2-[methylaminocarbonyl]-ethylthio)-penem-3-carboxylic acid, its pharmaceutically acceptable salts and esters as well as compositions containing them and methods for their use.

15 Claims, No Drawings

(5R, 6S, 8R-6-(1-HYDROXYETHYL)-2-(2-[METHYLAMINOCARBONYL]-ETHYLTHIO)-PENEM-3-CARBOXYLIC ACID

BACKGROUND OF THE INVENTION

This invention relates to 5R,6S,8R-6-(1-hydroxyethyl)-2-(2-[methylaminocarbonyl]-ethylthio)-penem-3-carboxylic acid and its pharmaceutically acceptable salts and esters, which compounds possess potent antibacterial activity.

There is a continuing need for a new antibacterial agents because continued extensive use of effective antibacterials gives rise to resistant strains of pathogens.

SUMMARY OF THE INVENTION 5R,6S,8R-6-(1-hydroxyethyl)-2-(2-[methylaminocarbonyl]-ethylthio)-penem-3-carboxylic acid and its pharmaceutically acceptable salts and esters possess antibacterial activity against both gram-positive and gram-negative bacteria.

DETAILED DESCRIPTION

When tested in standardized microbiological assays, the compounds of this invention are active against such gram-positive organisms as *Staphylococcus epidermis* and *Bacillus subtilis*, and such gram-negative organisms as *E. coli* and *Salmonella*, at test levels of 0.1 to 1.0 micrograms/ml. Additionally, they show activity against organisms which produce beta-lactamases, e.g., penicillinase and cephlosporinase, indicating a resistance against these enzymes. For instance, the sodium salt of 5R,6S,8R-6-(1-hydroxyethyl-2-(2[methylaminocarbonyl] ethylthio)penem-3-carboxylic acid is active against *Staphylococcus aureus* 76010501 at a test level of 0.25 microgram/ml. When tested against *E. coli* 74081501 (a beta-lactamase producing organism) the compound exhibits activity at 0.50 microgram/ml.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal and antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred. Typical pharmaceutically acceptable carries for use in the formulations described above are exemplified by: sugars such as lactose, sucrose, mannitol and sorbitol; starches such as corn starch, tapioco starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium sterate; vegetable oils such as peanut oil, cottonseed oil, sesame oil, olive oil and corn oil; nonionic, cationic and anionic surfactants; ethylene gylcol polymers; betacyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic) aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. For example, salts of the compound can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts of the compound are obtained in the usual manner, for example, by treating with an acid or a suitable anion exchange reagent. The esters are preparable in a manner analogous to the preparation of the corresponding esters of penicillins and cephalosporins.

The compounds of this invention are prepared by activating the allyl ester of 5R,6S,8R,2'RS-6(1-hydroxyethyl)-2-(2-ethylthio)penem-3-carboxylate (prepared as disclosed in European patent application No. 80810004.4, published July 23, 1980 as No. 0013662) to the sulfoxide and displacement at the 2-position with 3-mercapto-N-methylpropionamide followed by removal of the allyl group to form an alkali metal salt, preferably the sodium or potassium salt. Treatment with, e.g. tartaric acid, converts the salt to the carboxylic acid.

The following examples illustrate the preparation of the compounds and compositions of this invention.

EXAMPLE 1

Allyl-(5R,6S,8R,2'RS)-2-)Ethanesulfinyl)-6-(1-Hydroxyethyl)-Penem-3-Carboxylate

Stir at 0°–5° C. a solution of allyl-(5R,6S,8R,2'RS)-2-ethylthio-6-(1-hydroxyethyl)-penem-3-carboxylate (31.5 g) in ethyl acetate (200 ml) and dichloromethane (100 ml) and add over 0.5 hours a solution of m-chloroperoxybenzoic acid (80–85%; 22 g) in ethyl acetate (120 ml). After a further 0.5 hours, add the solution to a stirred mixture of ethyl acetate (150 ml), water (125 ml) and sodium bicarbonate (15 g), and stir rapidly for 15 mins. Dry the organic phase over $MgSO_4$, evaporate and chromatograph rapidly on silica gel, elute 1:1 hexame-ethyl acetate then pure ethyl acetate. Evaporate the product fractions and pump the residue at high vacuum to give the title compound as a thick yellow oil.

PMR ($CDCL_3$); $\delta$ 1.2–1.6 (m, 6H), 3.0–3.35 (m, 2H), 3.38 (br.s, 1H, exch Dy $D_2O$), 3.83 (m, 1H), 4.18 (m, 1H), 4.75 (br.d, J=6.5Hz), 5.2–5.6 (m, 2H), 5.73 and 5.89 (both d, J=1.5 Hz, total 1H) and 5.8–6.2 (m, 1H).

The compound obtained is a mixture of isomers which are diastereoisomeric at the oxidized sulfur. The mixture was used as such in the next step since both isomers react.

EXAMPLE 2

Allyl-(5R,6S, 8R)-6-(1-Hydroxyethyl)-2-(2-[Methylcarbamoyl]-Ethylthio)-Penem-3-Carboxylate Stir a solution of the penem allyl ester sulfoxide (2.55 g) prepared in Example 1 in $CH_2Cl_2$ (40 ml) with 3-mercapto-N-methylpropionamide (1.92 g) and cool to $-10°$ C. Add diisopropylethylamine (0.6 ml) and continue stirring at $-10°$ C. for 0.5 hour. Add ether (50 ml) and collect the precipitate and wash with ether. Stir the resulting solid with $CH_2Cl_2$ (20 ml) for 0.5 hour at 0° C., collect and dry to give the title compound as a white powder. m.p. 176°–178° C.

IR(nujol suspension): $v_{max}$ 3400, 3300, 1775, 1695, 1635, 1560 and 1510 $cm^{-1}$.

EXAMPLE 3

Sodium-(5R,6S,8R)-6-(1-Hydroxyethyl)-2-(2-Methylcarbamoyl]-Ethylthio-Penem-3-Carboxylate Stir a suspension/solution of the compound of Example 2 (0.66 g) in dry THF (50 ml) containing sodium 2-ethylhexanoate (0.305 g) and triphenylphosphine (0.12 g) at 25° C. under $N_2$ and add Pd $(PPh_3)_4$ (0.08 g). After 1.5 hour, add hexane (50 ml) and collect the crude product by centrifuge, wash with 2×20 ml ethyl acetate and partition with $H_2O$ (50 ml)—ethyl acetate (50 ml). Treat the aqueous phase with $N_2$ to remove dissolved organics then filter through 5 g of reverse phase C-18 silica gel, washing with $H_2O$. Treat the filtrate with 5 g of DARCO active carbon, stir 0.5 hour, filter, wash with $H_2O$ and lyophilize to give the product as a buff powder.

PMR ($D_2O$): $\delta$ 1.30 (d, J=7Hz; 3H), 2.63 (m; 2H), 2.72 (s; 3H), 3.14 (m; 2H), 3.91 (dd, J=1.5 and 8 Hz; 1H) 4.25 (pentet, J=8Hz; 1H) and 5.69 (d, J=1.5 Hz; 1H)

I claim:

1. 5R,6S,8R-6-(1-hydroxyethyl)-2-(2[methylaminocarbonyl]-ethylthio)-penem-3-carboxylic acid and the pharmaceutically acceptable salts and esters thereof.

2. The compound of claim 1 wherein the pharmaceutically acceptable salt is an alkali metal salt.

3. The compound of claim 1 wherein the pharmaceutically acceptable salt is an alkaline earth metal salt.

4. The compound of claim 1 wherein the pharmaceutically acceptable salt is an amine salt.

5. The compound of claim 1 wherein the pharmaceutically acceptable esters are metabolizable esters.

6. The compound of claim 2 wherein the alkali metal is sodium.

7. The compound of claim 2 wherein the alkali metal salt is potassium.

8. An antibacterially effective pharmaceutical composition comprising an antibacterial effective amount of a compound of claim 1 in admixture with a pharmaceutically acceptable carrier therefore.

9. A composition according to claim 8 adapted for oral administration.

10. A composition according to claim 8 adapted for parenteral administration.

11. A composition according to claim 8 adapted for topical administration.

12. A method of treating or preventing susceptible bacterial infections which comprises administering to a host in need of such treatment or prevention a compound of claim 1 or a pharmaceutical composition thereof in an amount sufficient to treat or prevent such infection.

13. A method according to claim 12 wherein the route of administration is oral.

14. A method according to claim 12 wherein the route of administration is parenteral.

15. A method according to claim 12 wherein the route of administration is topical.

* * * * *